United States Patent
Hoshino

(10) Patent No.: US 6,937,695 B2
(45) Date of Patent: Aug. 30, 2005

(54) ANALYZING APPARATUS AND ANALYZING METHOD

(75) Inventor: Kazuhito Hoshino, Saitama (JP)

(73) Assignee: Rigaku Corporation, Akishima (JP)

( * ) Notice: Subject to any disclaimer, the term of this patent is extended or adjusted under 35 U.S.C. 154(b) by 0 days.

(21) Appl. No.: 10/673,185

(22) Filed: Sep. 30, 2003

(65) Prior Publication Data

US 2004/0066895 A1 Apr. 8, 2004

(30) Foreign Application Priority Data

Oct. 2, 2002 (JP) ........................................ 2002-289501

(51) Int. Cl.⁷ .......................................... G01N 23/201
(52) U.S. Cl. .............................. 378/86; 378/88; 378/79; 250/281
(58) Field of Search .............................. 378/71, 79, 80, 378/82, 83, 86, 88; 250/281

(56) References Cited

U.S. PATENT DOCUMENTS 3,089,031 A    5/1963  Endter 5,528,032 A  *  6/1996  Uchiyama .................... 250/288

FOREIGN PATENT DOCUMENTS

| EP | 0 943 914 A2 | 9/1999 |
| GB | 2156974 A | 10/1985 |
| JP | 8-15185 | 1/1996 |
| JP | 10-19815 | 1/1998 |
| JP | 2000292375 | 10/2000 |

OTHER PUBLICATIONS

EPO Search Report dated Dec. 29, 2003, in EP Application No. 03256110.2–2204.

* cited by examiner

*Primary Examiner*—Edward J. Glick
*Assistant Examiner*—Chih-Cheng Glen Kao
(74) *Attorney, Agent, or Firm*—Burns, Doane, Swecker & Mathis LLP

(57) ABSTRACT

Provided are an analyzing apparatus and an analyzing method for analyzing a sample by performing measurements using X-rays and measuring a gas generated from the sample.

8 Claims, 14 Drawing Sheets

ANALYZING APPARATUS AND ANALYZING METHOD

BACKGROUND OF THE INVENTION

1. Field of the Invention

The present invention relates to an analyzing apparatus and an analyzing method, both for analyzing a sample by performing measuring by using X-rays and measuring about the gas generated from the sample.

2. Description of the Related Art

Various X-ray apparatuses have been known, which are designed to determine the molecular structures of samples. Among these apparatuses are the X-ray diffraction apparatus, the X-ray scattering apparatus and the small-angle X-ray scattering apparatus. Any one of these X-ray apparatuses has an X-ray detector that detects the diffracted X-rays or scattered X-rays generated from a sample when X-rays are applied to the sample. This detector's operation makes it possible to measure the angle of the X-rays generated from the sample, e.g., diffraction angle, and the intensity of the X-rays. The results of measuring are plotted on a coordinate graph, thus providing an X-ray diffraction diagram known as X-ray diffraction profile. Various data items about the sample, such as the molecular structure of the sample, can be obtained from the X-ray diffraction profile.

The molecular structure of an object changes with the temperature at which it is set. How the molecular structure changes as the temperature varies can be determined by observing how the peak in the X-ray diffraction profile changes in position and value. The change in the molecular structure of the object, thus determined, may help to select the object for a specific use and to develop materials for particular purposes.

The position and value of the peak in the X-ray diffraction profile about a sample do not depend on only the change in the molecular structure of the sample. Rather, they may on other factors, such as decomposition (e.g., pyrolysis) of the sample, too. If we perform X-ray diffraction analysis on a sample, believing that the peak in the X-ray diffraction profile changes in position solely due to the change in the molecular structure of the sample, we may make an error in deciding a possible use of the material.

In view of this, it is necessary to use an apparatus that determine whether the sample has undergone decomposition. We may use the mass spectrometer. The mass spectrometer can determine the mass number of the gas generated from the sample. Hence, the mass spectrometer can identify the elements contained in the gas. If the X-ray diffraction analysis mentioned above is combined with the mass analysis, the sample will be analyzed more reliably.

Hitherto, many sample-analyzing methods have been proposed, each a combination of two or more analyses. Japanese Patent Laid-Open Publication No. H10-019815 discloses a method that is a combination of pyrolysis analysis and X-ray diffraction analysis. Japanese Patent Laid-Open Publication No. 8-015185 discloses a method that is a combination of X-ray diffraction analysis and another analysis, such as mass analysis.

The change in the molecular structure of a sample and the decomposition of the sample can be distinguished from each other, by observing both the X-ray diffraction profile based on the results obtained by the use of an X-ray apparatus and the data about the gas, obtained by the use of an mass spectrometer. In other words, it can be determined which, a change in the molecular structure of the sample or the pyrolysis of the sample, has changed the position and value of the peak in the X-ray diffraction profile.

However, no analysis has been practiced, using simultaneously both an X-ray analysis apparatus and any other analysis apparatus such as the mass spectrometer. No method has been known, in which both the X-ray diffraction analysis and the mass analysis are carried out on the same sample at the same time, while changing the temperature of the sample. It has been extremely difficult to perform various analyses on a sample in the same condition, in an attempt to analyze the sample while changing its temperature.

SUMMARY OF THE INVENTION

The present invention has been made in view of the foregoing. An object of the invention is to provide an analyzing apparatus and analyzing method that can accurately determine the cause of changes, if any, in the characteristics of a sample as the temperature of the sample varies.

To attain the object, an analyzing apparatus according to the present invention comprises: an X-ray measuring means for applying X-rays to a sample and detecting X-rays generated by the sample; a gas-analyzing means for analyzing gas generated by the sample; a sample-holding means for holding the sample at a position which is common to the X-ray measuring means and the gas-analyzing means; a sample temperature-controlling means for controlling a temperature of the sample; and a control means for controlling the X-ray measuring means and the gas-analyzing means, causing the same to detect the X-rays and analyze the gas at the same time.

The analyzing apparatus can determine the characteristics of the sample from the X-ray diffraction profile obtained from the results of the measuring performed by the X-ray measuring means and from the data about the sample, acquired by the gas-analyzing means. Hence, the apparatus helps to identify the sample accurately even if the sample is of such a type that cannot be identified correctly by using the X-ray diffraction profile only or by employing the gas-analyzing means only.

In the analyzing apparatus, the sample remains at the same position while both the X-ray measuring means and the gas-analyzing means. Hence, the X-rays and gas generated from the sample can be analyzed at the same time and in the same condition. The data obtained by detecting the X-rays and the data obtained by analyzing the gas therefore pertain to the same sample and acquired at the same time and in the same condition. This makes it easy to whether the molecular structure of the sample is changing. It is therefore possible to determine whether the sample is decomposing or a part of the sample is being liberated.

Thanks to the use of the sample temperature-controlling means, the sample can be analyzed while its temperature is being changed. Although the temperature of the sample is so changed, the sample remains in the same condition, when the X-rays are being detected and the gas is being analyzed.

Suppose the sample is held in one chamber (at one position) while the X-ray measuring means is detecting the X-rays, and in another chamber (at another position) while the gas-analyzing means is analyzing the gas. Then, the data acquired must be corrected on the basis of the sizes of the respective chambers, the temperatures that the sample has in these chambers, respectively, and the individual properties of the sample, and the like. Such correction of data is unnecessary in the present invention. The analyzing apparatus of this invention can yet acquire reliable data about the sample.

The gas-analyzing means may be, for example, a mass spectrometer, an IR (Infrared Spectrophotometer), or the like. The temperature-controlling means may be a heater for heating the sample. If so, the sample may be an organic compound, such as the material of ion-exchange film, that should be set at high temperatures during an in-situ analysis.

In the analyzing apparatus, the X-ray measuring means may be a small-angle X-ray scattering device that can detect X-rays scattered at small angles. The small-angle X-ray scattering device may be one configured to detect an X-ray scattered at a small angle to the axis of an X-ray applied to it. This device detects X-rays scattered at a small angle, which a wide-angle goniometer cannot detect. The small angle ranges from about 0.1° to 5°, preferably from about 0.1° to 4°.

To detect X-rays scattered at such small angles to enhance the resolution in such a narrow range of scattering angle, the small-angle X-ray scattering device may have various structure features that differ from those of the ordinary X-ray diffraction apparatus designed to deal with X-rays scattered at angles in a broad range. Among the various structural features are: (1) X-rays are applied in the form of parallel narrow beams; (2) a plate having several slits, for example three slits, is arranged on the optical path to prevent unnecessary, parasitic scattered rays from reaching the sample; (3) the X-ray path extending from the X-ray source to the X-ray measuring means (i.e., X-ray detector) is held in a vacuum; (4) the distance between the sample and the X-ray measuring means (i.e., X-ray detector), or so-called "camera length" is very long.

The small-angle X-ray scattering device can serve to provide an X-ray diffraction profile that helps to determine the molecular structure of materials having long-period structures, such as organic compounds. Note that no wide-angle X-ray apparatuses can provide such X-ray diffraction profiles.

In the analyzing apparatus described above, the gas-analyzing means may be a mass spectrometer that can detect the mass number of the gas generated from the sample. The analyzing apparatus can, therefore, identify the elements contained in the gas. From the elements identified it can be easily determined whether the sample has undergone pyrolysis or partial liberation. Thus, it can be easily determined whether the change in the position and value of the peak in the X-ray diffraction profile has resulted from the change in the molecular structure of the sample or from the change accompanying the decomposition of the sample or the liberation of the elements of the gas.

In the analyzing apparatus, the sample-holding means may hold the sample and be arranged on the X-ray path in the X-ray measuring means, the X-rays may be applied to the sample held in the sample-holding means, the X-rays generated by the sample may be emitted outside the sample-holding means, and the gas generated from the sample may be preferably discharged outside the sample-holding means.

In the analyzing apparatus, the sample-holding means may preferably have an annular member that has a space for holding the sample, a pair of shield members that contact the front and back sides of the annular member and shield the space from outside, and a gas passage that connects the space in the annular member to the space outside the annular member. In this case, the sample-holding means can be very simple in structure and can steadily hold the sample while the sample is being analyzed, only if it is located between the X-ray measuring means and the gas-analyzing means.

In the analyzing apparatus described above, the gas passage may be one that guides carrier gas and the gas generated from the sample. Then, the gas generated from the sample can be reliably discharged from the sample-holding means.

The analyzing apparatus described above may further comprise a pressing means that presses the shield members onto the annular member, for the following reason. To keep the shield members in contact with the front and back sides of the annular member, adhesive or bonding agent may be applied. If adhesive is used, however, the solvent contained in the adhesive will evaporate and mix with the gas generated from the sample. This makes it impossible to analyze the gas with desired accuracy. Since the shield members are set in contact with the annular member by the mechanical means, not using adhesive at all, no impurity gas is generated. The gas generated from the sample can, therefore, be analyzed with high accuracy.

In the analyzing apparatus described in the preceding paragraph, the pressing means may press the shield members to the annular member, with a heat-resistant rubber layer interposed between each shield member and the annular member. If so, the shield members can reliably contact the annular member, owning to the resilient force of the rubber layers. Moreover, the rubber layers apply a constant pressure to the shield members even if the sample is heated to a high temperature, because the rubber layers are resistant to heat. Hence, the sample can be held in constant conditions, though it is repeated heated and cooled.

In the analyzing apparatus described above, the shield members may be made preferably of polyimide film. This is because polyimide film is transparent to X-rays, resistant to heat and scarcely emit gases. Its characteristics remain stable at high temperatures, up to about 400° C.

In the analyzing apparatus described above, the X-ray measuring means may preferably have a two-dimensional X-ray detector that detects the X-rays generated from the sample. The two-dimensional X-ray detector is a device that can receive light in a plane and can detect X-rays at various points in that plane. It may be, for example, an X-ray detector that uses an X-ray plate, an X-ray film, a storage phosphor or a CCD (Charge Coupled Device) sensor.

The two-dimensional X-ray detector can detect X-rays faster than the 0th-order X-ray detector or the linear X-ray detector. The two-dimensional X-ray detector is desirable for use in measuring X-rays in analyzing the sample, that is, in the in-situ analysis. This is because this detector can detect the X-rays emanating from the sample even if the sample undergoes an abrupt structure change while it is used in practice.

In the analyzing apparatus described above, the X-ray measuring means may preferably have an X-ray-collecting means that collects X-rays before applying the X-rays to the sample. The X-ray-collecting means may be an X-ray optical element that can focus an X-ray at one point. More specifically, it may be a con-focal mirror that reflects X-rays, or an X-ray-collecting element that diffracts X-rays.

In any ordinary X-ray optical system that has no X-ray-collecting means, the X-rays applied to the sample (i.e., object to be measured) have low intensity. The X-ray-collecting means focuses each X-ray to be applied to the sample. Thus, the sample can be irradiated with intense X-rays.

With an X-ray measuring apparatus of ordinary structure, which uses low-intensity X-rays, it takes a very long time to provide an X-ray diffraction profile. By contrast, the X-ray measuring means, which has the X-ray-collecting means, can apply high-intensity X-rays to the sample and can, therefore, provide an X-ray diffraction profile within a very short time. This renders the analyzing apparatus appropriate for use in in-situ analysis.

In the analyzing apparatus described above, the X-ray-collecting means may preferably be a con-focal mirror. Note that a con-focal mirror is an X-ray reflecting mirror that has at least two X-ray reflecting surfaces intersecting with each other, preferably at right angles. The mirror is so designed that the X-rays reflected from the X-ray reflecting surfaces meet at the same focal point or at focal points very close to one another.

The con-focal mirror may comprise only one layer of material that provides an X-ray reflecting surface capable of reflecting or diffracting X-rays. Alternatively, it may comprise a plurality of layers of material that can reflect or diffract X-rays. The multi-layer con-focal mirror can provide more intense X-ray beams than the single-layer con-focal mirror and therefore serves to shorten the measuring time.

In the analyzing apparatus described above, it is desired that the X-ray measuring means should have a point-focus X-ray source. The term "point focus" is used in contrast to "line focus". "Point focus" pertains to X-rays that have a square cross section having four sides of substantially the same length, forming a square light spot on the sample. By contrast, the term "line focus" pertains to X-rays that have a rectangular cross section, thus forming an elongated light spot on the sample.

More precisely, the point-focus X-ray source emits X-ray beams, each forming, on the sample, a circular light spot having a diameter of, for example, about 0.3 mm or a square light spot having a size of about 0.3 mm×about 0.3 mm.

If a line-focus X-ray source is used, those parts of the rectangular light spot which lie outside each tiny light-receiving region of the sample will be wasted, not contributing to the measuring of the X-ray. This means that the line-focus X-ray source cannot apply sufficiently intense X-rays to the sample. By contrast, any X-ray emitted from the point-focus X-ray source is applied, in its entirety, to one tiny light-receiving region of the sample. Thus, the point-focus X-ray source can apply sufficiently intense X-rays to the sample. This helps to shorten the measuring time further.

Another analyzing apparatus according to this invention comprises: an X-ray measuring means for applying X-rays to a sample and detecting X-rays generated by the sample; a gas-analyzing means for analyzing gas generated by the sample; a sample-holding means for holding the sample at a position which is common to the X-ray measuring means and the gas-analyzing means; and a control means for controlling the X-ray measuring means, causing the same to detect the X-rays, in accordance with the results of analysis performed by the gas-analyzing means, or for controlling the gas-analyzing means, causing the same to analyze the gas, in accordance with the results of measuring performed by the X-ray measuring means.

With this analyzing apparatus, unnecessary measuring can be omitted or the conditions for detecting X-rays or analyzing the gas can be changed, once the X-ray measuring means has detected X-rays or the gas-analyzing means has analyzed the gas. This prevents the wasting of time. If it is found no longer necessary to detect X-rays or analyze the gas, unnecessary measuring can be omitted thereafter, which saves time.

In this analyzing apparatus, the control means can stop the X-ray measuring means in accordance with the results of analysis performed by the gas-analyzing means, and can stop the gas-analyzing means in accordance with the results of measuring performed by the X-ray measuring means. Thus, unnecessary X-ray detection and unnecessary gas analysis can be avoided, thus saving time.

In this analyzing apparatus, the control means can stop the measuring performed by the X-ray measuring means, when the gas-analyzing means detects a particular gas.

Thus, if the sample generates any gas that impairs the measuring, the measuring can be stopped at once to ensure safety. If any gas detected indicates that the sample has undergone a specific reaction, the measuring is stopped immediately. That is, the measuring is interrupted whenever necessary.

The analyzing apparatus described above may further comprises a sample temperature-controlling means for controlling a temperature of the sample. In this case, the control means may preferably change a condition of controlling the temperature of the sample, in accordance with results of the measuring performed by the gas-analyzing means and/or results of the measuring performed by the X-ray measuring means. Thus, measuring under the unnecessary conditions can be omitted, which shorten the measuring time on various conditions.

In the analyzing apparatus, the sample may be an ion-exchange film or an organic compound. Organic compounds have long-period structures and can hardly be measured by the wide-angle X-ray apparatus generally used as X-ray measuring apparatus. The analyzing apparatus according to this invention can analyze the molecular structure of such an organic compound, because it comprises a small-angle scattering device as X-ray measuring means. In the present invention, the X-ray detector may be a two-dimensional X-ray detector, X-ray focusing means may be provided in the X-ray path extending to the sample, and the X-ray source is a point-focus source. Therefore, a high-intensity X-ray can therefore be applied to the sample, and the scattered X-ray generated from the sample can be detected in a plane. Hence, the analyzing apparatus of the present invention can perform measuring on organic compounds within a very short time.

Ion-exchange film is a high-molecular compound. In recent years, it is used as main component of fuel cells. When used in a fuel cell, the ion-exchange film remains wetted (i.e., at the humidity of 100%) in most cases. To perform in-situ analysis on the ion-exchange film, it is demanded that small-angle scattering measuring be carried out within a short time at high temperatures. The analyzing apparatus according to the present invention can fully meet this demand.

DETAILED DESCRIPTION OF THE PREFERRED EMBODIMENTS

An analyzing apparatus according to the present invention will be described. The apparatus comprises a small angle X-ray scattering device and a mass spectrometer. The small-angle x-ray scattering device and the mass spectrometer function as an X-ray measuring means and second measuring means. The analyzing apparatus is no more than one embodiment of the invention, not limiting the present invention.

Figure 1:
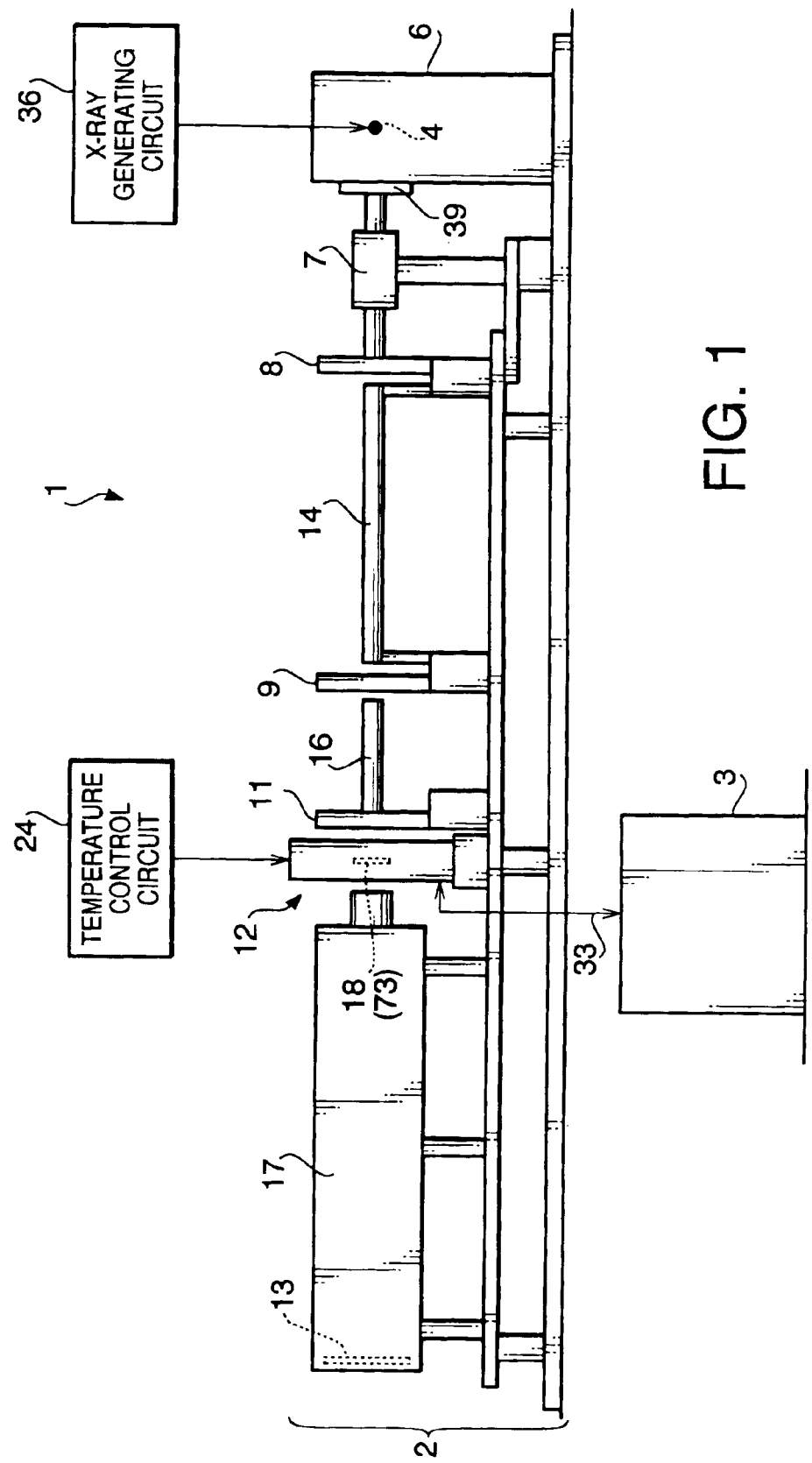
FIG. 1 is a front view showing an analyzing apparatus according to an embodiment of the present invention.

FIG. 1 shows the mechanical configuration of the analyzing apparatus 1. The analyzing apparatus 1 has a small-angle X-ray scattering device 2 and a mass spectrometer 3. The small-angle X-ray scattering device 2 is used as the X-ray measuring means, and the mass spectrometer 3 as the second measuring means.

The small-angle X-ray scattering device 2 comprises an x-ray tube 6, a con-focal mirror 7, a first slit 8, a second slit 9, a third slit 11, a sample holder 12, and a two-dimensional X-ray detector 13. The X-ray tube 6 has an X-ray source 4. The con-focal mirror 7 functions as an X-ray-collecting means for focusing the X-ray generated by the X-ray source 4, at one focal point. The sample holder 12 functions as a sample-holding means. The two-dimensional X-ray detector 13 functions as an X-ray detecting means. The detector 13 is a phosphor plate that has a storage phosphor layer formed on the X-ray detecting surface.

Figure 2:
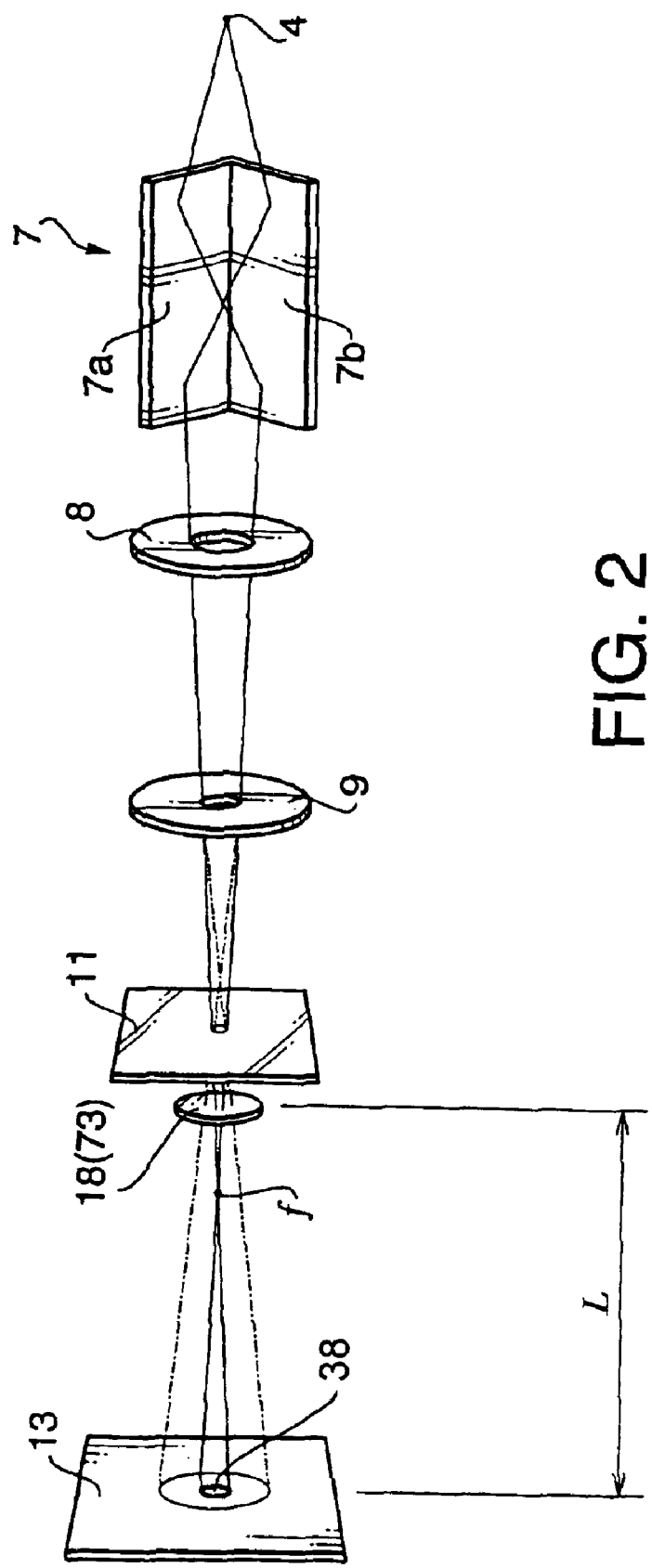
FIG. 2 is a schematic representation of the optical system incorporated in the X-ray apparatus shown in FIG. 1.

FIG. 2 is a schematic diagram illustrating how an X-ray propagates in the small-angle X-ray scattering device 2 shown in FIG. 1. In FIG. 2, the components identical to those shown in FIG. 1 are designated at the same reference numerals. As FIG. 2 shows, the con-focal mirror 7 has two X-ray reflecting surfaces 7a and 7b that intersect with each other at right angles. The mirror 7 is an X-ray reflecting mirror that is designed such that the X-rays reflected by the surfaces 7a and 7b reach the same focal point "f" or points close to one another.

The con-focal mirror 7 is a single-layer mirror. It may be made of material that can reflect X-rays, such as nickel, platinum, tungsten, or the like. Alternatively, the mirror 7 may be a multi-layer mirror that has an X-ray reflecting surface and comprises a plurality of thin films laid on the reflecting surface, one upon another. In this case, the mirror 7 reflects X-rays by virtue of the diffraction of X-rays. Note that a multi-layer mirror can reflect and focus a more intense X-ray at the focal point "f" than a single-layer mirror.

As FIG. 1 illustrates, a tube 14 is arranged between the first slit 8 and the second slit 9, and a tube 16 is provided between the second slit 9 and the third slit 11. Further, a tube 17 is arranged downstream of the sample holder 12 (namely, on the left side of FIG. 1). The two-dimensional X-ray detector 13 is set within one end of the tube 17. The tubes 14, 16 and 17 are connected to a vacuum device (not sown) and depressurized to a vacuum or almost to a vacuum.

The small-angle X-ray scattering device 2 of this embodiment is configured to detect the scattered radiation emanating from the sample 18 held by the sample holder 12. The scattered radiation has a very small intensity. It is therefore necessary to prevent the X-rays scattered by air from disturbing the light beam emanating from the sample 18. To this end, the tubes 14, 16 and 17 are arranged as specified above, thus constituting a vacuum path.

Figure 4:
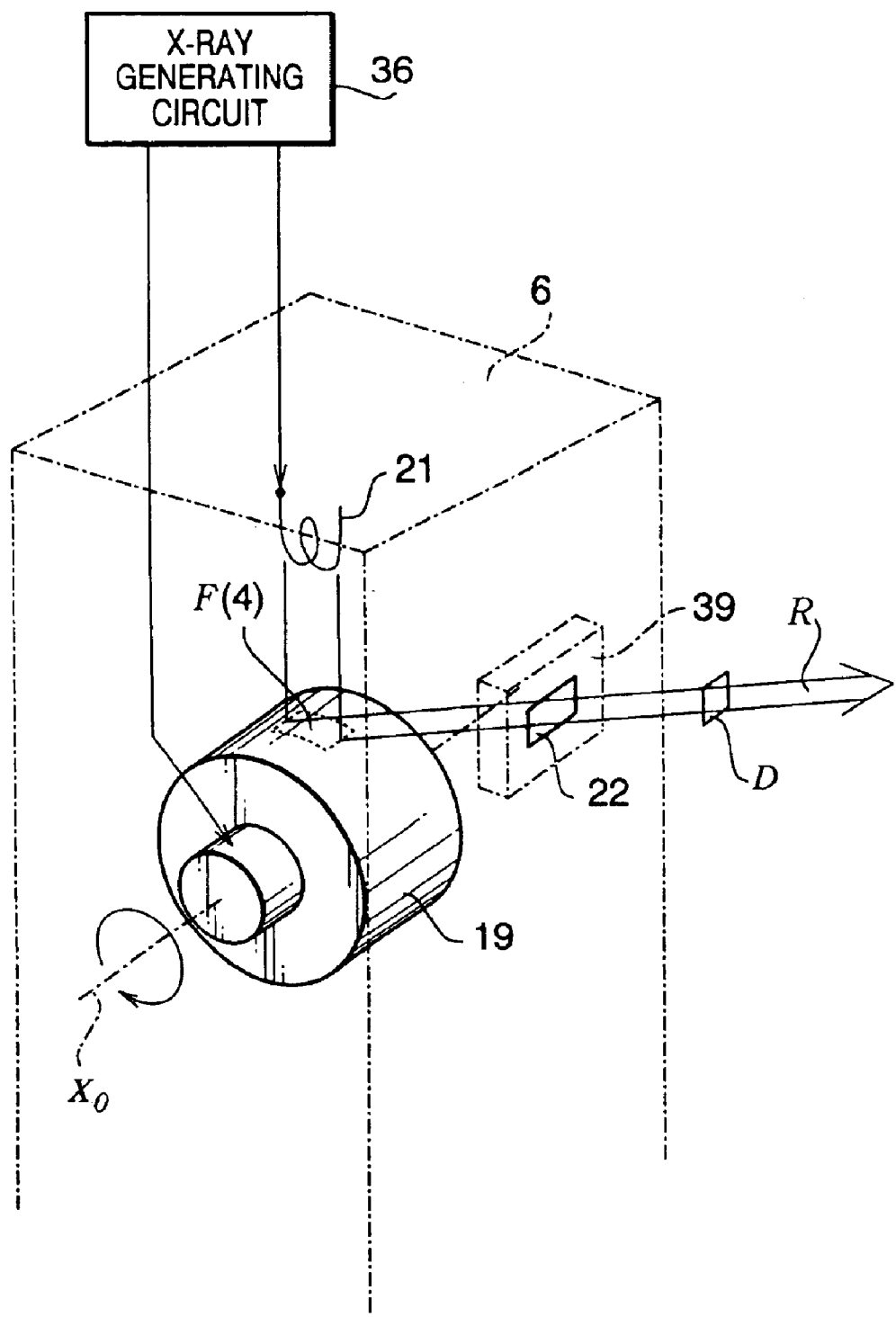
FIG. 4 is a perspective view depicting the internal structure of the X-ray tube provided in the X-ray small-angle scattering device shown in FIG. 1.

The X-ray tube 6 used in this embodiment should be one that can generate as intense X-rays as possible, so that the sample 18 may be analyzed fast. This is why the X-ray rube 6 comprises a rotor target 19 and a filament 21, as is illustrated in FIG. 4. The rotor target 19 incorporates a cooling unit and can rotate at high speed. The filament 21 can apply a high voltage between it and the target 19.

As seen from FIG. 1, an X-ray generating circuit 36 is connected to the X-ray tube 6. The circuit 36 supplies a predetermined current to the filament 21 and applies a prescribed voltage, so-called "tube voltage", between the rotor target 19 and the filament 21. The circuit 36 detects the current flowing in the target 19, known as "tube current". Further, the X-ray generating circuit 36 controls the current supplied to the filament 21 to maintain the tube current at a constant value. In this embodiment, the tube voltage is 45 kV, and the tube current is −60 mA.

The filament 21 is heated and emits thermoelectrons when an electric current flows through it. The thermoelectrons emitted from the filament 21 are accelerated, by virtue of the high voltage applied between the target 19 and the filament 21. The thermoelectrons thus accelerated impinge upon the surface of the target 19. The region "F" in which the thermoelectrons impinge is an X-ray focus "F", at which an X-ray is generated. That is, the X-ray focus "F" is an X-ray source 4. The X-ray source 4 can generate a point-focused X-ray in the present embodiment.

The X-ray focus "F" is rectangular as in most cases. An X-ray is acquired at a short side of the rectangular X-ray focus "F" in the present embodiment. More precisely, the X-ray is emitted outside of the X-ray tube 6 through an X-ray window 22 located at the short side of the X-ray focus "F". The X-ray "R" thus emitted has a cross section "D" that is square, almost square, circular, or almost circular. Since the X-ray thus emitted has such a cross section, the X-ray focus "F" is called "X-ray focus of point type."

The X-ray may be emitted from a long side of the rectangular X-ray focus "F". In this case, the X-ray "R" emitted has a rectangular cross section. Hence, the X-ray focus "F" is called "X-ray focus of line type". The X-ray window 22 is covered with an X-ray shutter 39, which can be opened and closed. The X-ray shutter 39 is driven by an appropriate drive means, such as an electric motor or an electromagnetic solenoid.

In the present embodiment, the X-ray tube 6 is depressurized to a vacuum or almost a vacuum and the rotor target 19 is rotated at high speed around its axis X0. Further, cooling water is circulated in the target 19. The surface of the target 19 is cooled as the target 19 is rotated at high speed and the cooling water flows in the target 19. This helps to supply many electrons to the X-ray focus "F". As a result, an X-ray of high intensity can be generated at the X-ray focus "F". The surface of the target 19 may be, for example, a Cu (copper) layer.

The slits 8, 9 and 11 provided in the small-angle X-ray scattering device 2 shown in FIG. 1 may have various shapes, rectangular, circular (pinhole), and the like. In this embodiment, the first, second and third slits 8, 9 and 11 are pinholes as shown in FIG. 2. The pinholes are desirable slits since the point-focus X-ray source 4 generates a point-focused X-ray and the mirror 7 is a con-focal mirror in the present embodiment.

Figure 5:
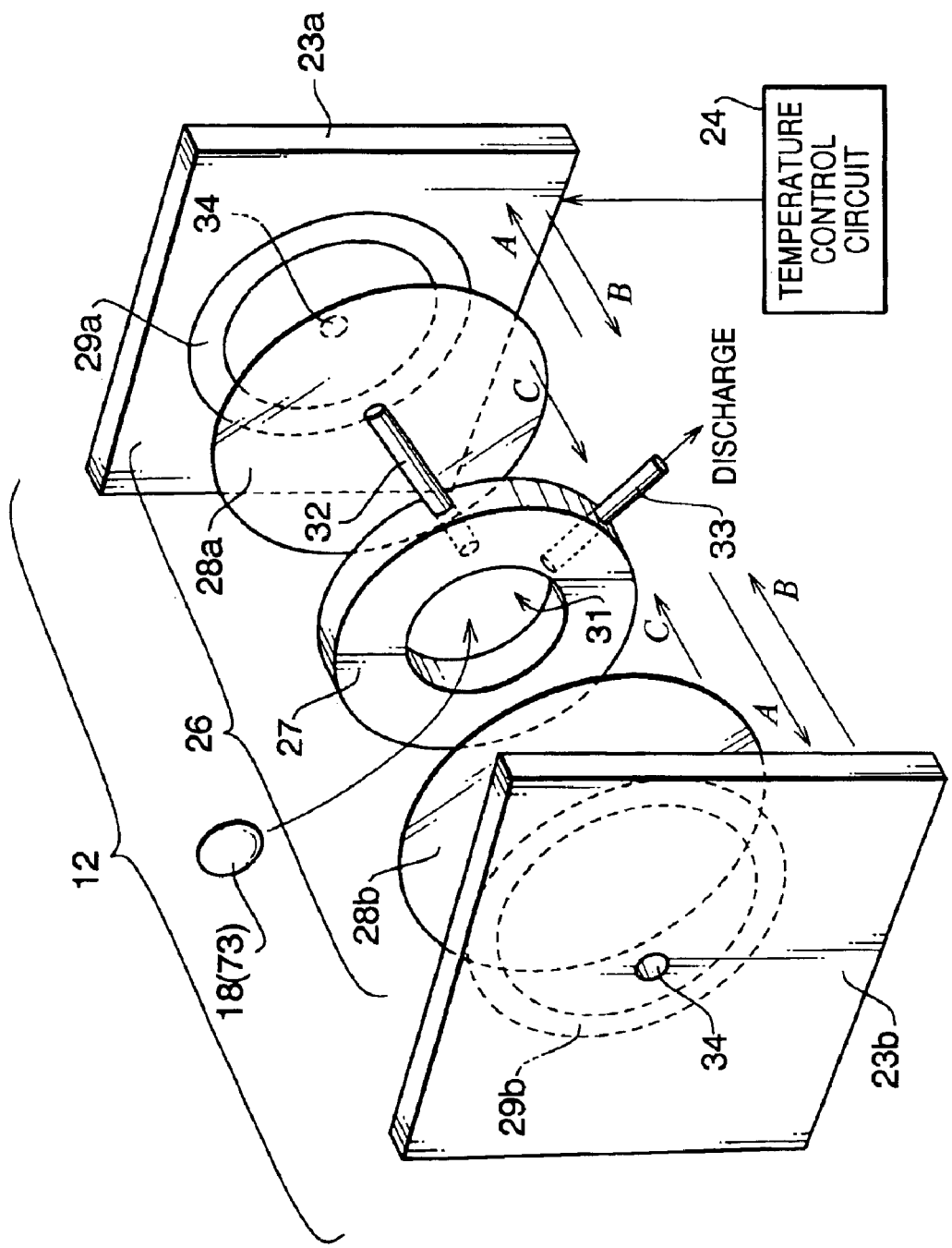
FIG. 5 is a perspective view of the sample-supporting device that constitutes the X-ray small-angle scattering device shown in FIG. 1.

As FIG. 5 shows, the sample holder 12 illustrated in FIG. 1 has a pair of heat plates 23a and 23b that function as sample-heating means. The heat plates 23a and 23b can move away from each other in the direction arrows "A" and toward each other in the directions of arrows "B", when driven by an opening-closing mechanism (not shown). The sample-heating means is not limited to the heat plates 23a and 23b. It can be replaced by a sample-heating means of any other structure.

The heat plate 23a or the heat plate 23b, or both contain a member that generates heat when an electric current flows through it. The heat-generating member is, for example, an electric heating wire. The heat-generating member is connected to a temperature control circuit 24. The circuit 24 controls the current supplied to the heat-generating member, thus changing the amount of heat that the heat plate 23a or the heat plate 23b, or both generate. Note that the heat plate 23a or the heat plate 23b, or both have an inner surface that radiates heat.

The heat plates 23a and 23b clamp a sample chamber assembly 26, with their inner surfaces (i.e., heat-radiating surfaces) set in direct contact with the sample chamber assembly 26. Preferably, the heat plates 23a and 23b firmly hold the assembly 26 by using elastic bias means such as springs, thus preventing the sample chamber assembly 26 from moving.

The sample chamber assembly 26 has an annular member 27 and shields 28a and 28b. The shields 28a and 28b are adhered to the sides of the annular member 27. The annular member 27 is made of, for example, brass and has a thickness of, for example, about 1 mm. The annular member 27 has a gas intake port 32 and a gas exhaust port 33, each opening at the inner and outer circumferences of the member 27. The gas intake port 32 is connected to a gas source (not shown). Carrier gas, or inert gas such as "He", is supplied through the gas intake port 32 into an inner space 31 defined by the annular member 27. The gas exhaust port 33 is connected to the gas intake port of the mass spectrometer 3 as illustrated in FIG. 1.

The shields 28a and 28b are flexible films and made of material that is transparent to X-rays and exhibits a great mechanical strength. The material may be, for example, polyethylene terephthalate such as Mylar (trade name), polyimide such as Capton (trade name), or the like. In FIG. 5, the shields 28a and 28b are presented as discs. Instead, they may be rectangular instead, or may have any other desirable shape.

Two ring-shaped, heat-resistant elastic members are provided, one interposed between the shield 28a and the heat plate 23a, and the other interposed between the shield 28b and the heat plate 23b. The heat-resistant elastic members are, for example, heat-resistant rubber rings 29a and 29b. The rings 29a and 29b press the shields 28a and 28b onto the front and back sides of the annular member 27, respectively, when the heat plates 23a and 23b are moved in the directions of arrows "B". As a result, the inner space 31 defined by the annular member 27 is shielded from the outside, though the gas intake port 32 and gas exhaust port 33 remain open to the outside. The sample 18 to be analyzed is inserted into the inner space 31 before the shields 28a and 28b are pressed onto the front and back sides of the annular member 27.

Made of the above-mentioned material such as polyimide, the shields 28a and 28b adhere to the annular member 27 once they are placed on the front and back sides of the member 27 in the directions of arrows "C". In view of this, the heat-resistant rubber rings 29a and 29b need not press the shields 28a and 28b in some cases. Nonetheless, it should be better to use the rubber rings 29a and 29b in order to accomplish a flawless analysis of the sample 18.

The shields 28a and 28b may be fastened to the annular member 27 by applying an adhesive or a bonding agent. The use of adhesive should be avoided as much as possible. This is because adhesive may generate unnecessary gas during the analysis of the sample 18. Unnecessary gas, if generated, would jeopardize the analysis of the gas generated from the sample 18. In the present embodiment, the heat-resistant rubber rings 29a and 29b fasten the shields 28a and 28b onto the annular member 27, not using adhesive at all. Hence, no unnecessary gas will be generated.

The sample chamber assembly 26 that defines the inner space 31 for accommodating the sample 18 is clamped between the heat plates 23a and 23b. Hence, the air in the inner space 31 is heated as the plates 23a and 23b radiate heat. The sample 18 placed in the space 31 is therefore heated.

The heat plates 23a and 23b have a through hole 34 each, in their center parts. One of the holes 34 allows passage of the X-rays being applied to the sample 18. The other hole 34 allows passage of the scattered radiation emanating from the sample 18.

The mass spectrometer 3 shown in FIG. 1 is a device that samples gas, if any, generated from the sample 18 held at a prescribed position by the sample holder 12 and flowing through the gas exhaust port 33 of the annular member 27. The mass spectrometer 3 measures the mass number of the gas thus sampled. It may be of any type available, so long as it can sample gas and measure the mass number of the gas.

The mass spectrometer 3 can perform measuring on the sample 18 held by the sample holder 12 at the sample position that lies on the X-ray path in the small-angle X-ray scattering device 2. The sample position is common to the small-angle X-ray scattering device 2 and the mass spectrometer 3.

The mass spectrometer 3 is employed not only to detect the X-rays the sample 18 scatters at small angles, but also to measure other characteristics of the sample 18. Therefore, the mass spectrometer 3 may be replaced by another measuring device, such as an IR (Infrared Spectrophotometer).

Figure 6:
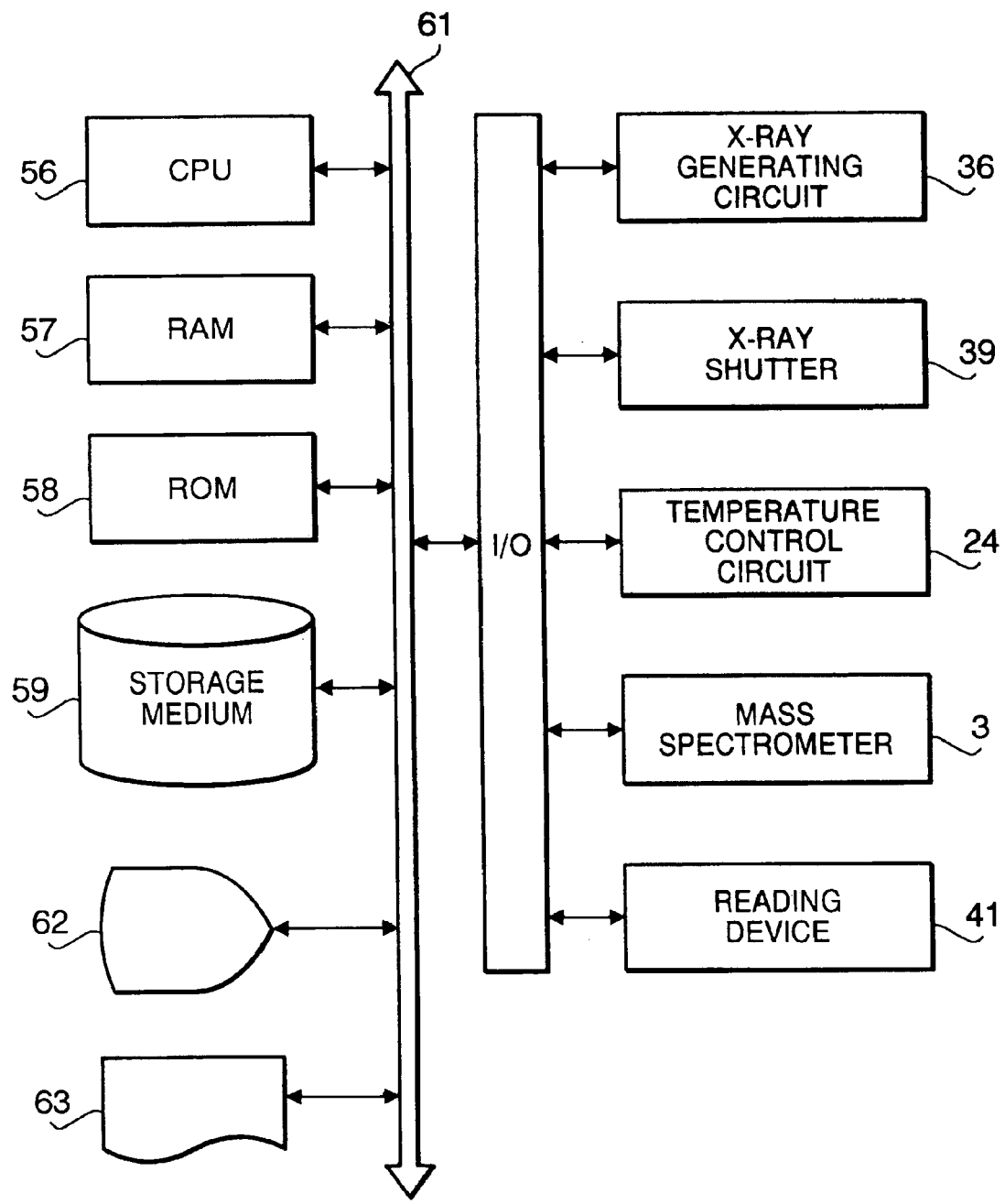
FIG. 6 is a block diagram showing a control system for use in the analyzing apparatus of FIG. 1.

FIG. 6 is a block diagram showing a control apparatus that may be used in the analyzing apparatus to control the above-mentioned components. The control apparatus is a computer system that comprises a CPU (Central Processing Unit) 56, a RAM (Random Access Memory) 57, a ROM (Read Only Memory) 58, and a storage medium 59. The storage medium 59 is a CD (Compact Disc), a DVD (Digital Video Disc), a hard disk, or the like. It stores a program that enables the small-angle X-ray scattering device 2 to analyze the sample 18 and a program that enables the mass spectrometer 3 to measure the mass number of the gas generated from the sample 18.

A bus 61 connects a display 62 and a printer 63 to the CPU 56. The display 62 is, for example, a cathode-ray tube or a liquid crystal display and displays data. The printer 63 prints the data. An input/output interface I/O connects the mass spectrometer 3, temperature control circuit 24, X-ray generating circuit 36 and X-ray shutter 39 to the bus 61. Thus, these devices 3, 24, 36 and 39 are connected to the CPU 56.

The CPU 56 executes the programs recorded in the storage medium 59, controlling the above-mentioned devices. These devices cooperate to perform, at the same time, small-angle X-ray scattering measurement and mass analysis on the sample 18 held by the sample holder 12.

In this embodiment, one computer system controls various devices. Nonetheless, several computers may be used to carry out the small-angle X-ray scattering measurement, the mass analysis, the temperature control and the like, respectively. If this is the case, a network may connect them, and the other computers connected to the network may include a server that perform the main data processing.

How the analyzing apparatus thus configured operates will be described, on the assumption that the sample 18 is an ion-exchange film that is an organic compound. The ion-exchange film is used as main component of fuel cells in recent years. Its molecular structure that changes with temperature variation and its temperature dependency that affects chemical changes such as pyrolysis and partial liberation are attracting much attention.

Figure 14:
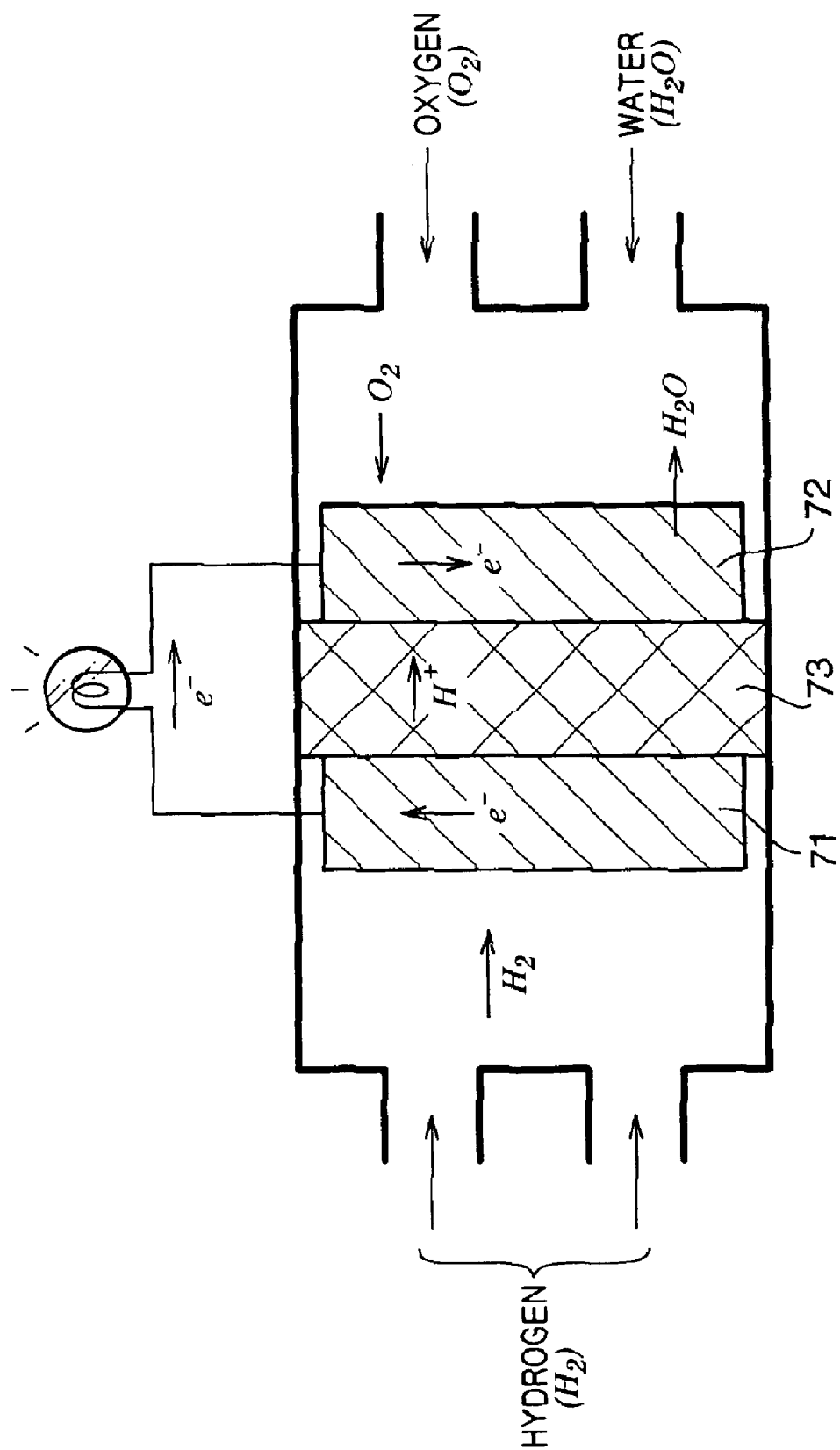
FIG. 14 is a schematic representation of a fuel cell.

As FIG. 14 shows, a fuel cell comprises a pair of electrodes, or fuel pole 71 and air pole 72, and an ion-exchange film 73 interposed between the poles 71 and 72. Hydrogen ($H_2$), i.e., the fuel, is supplied from the fuel pole 71 to the ion-exchange film 73. Oxygen ($O_2$) is supplied from the air pole 72 to the ion-exchange film 73.

In the fuel cell, hydrogen and oxygen undergo the following chemical reaction:

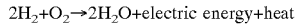
$$2H_2 + O_2 \rightarrow 2H_2O + \text{electric energy} + \text{heat}$$

This is a chemical reaction that is invert to the electrolysis of water. The reaction yields electric energy. The heat generated along with the electric energy can be absorbed by an appropriate cooling method in which the cooling water is circulated.

Figure 12:
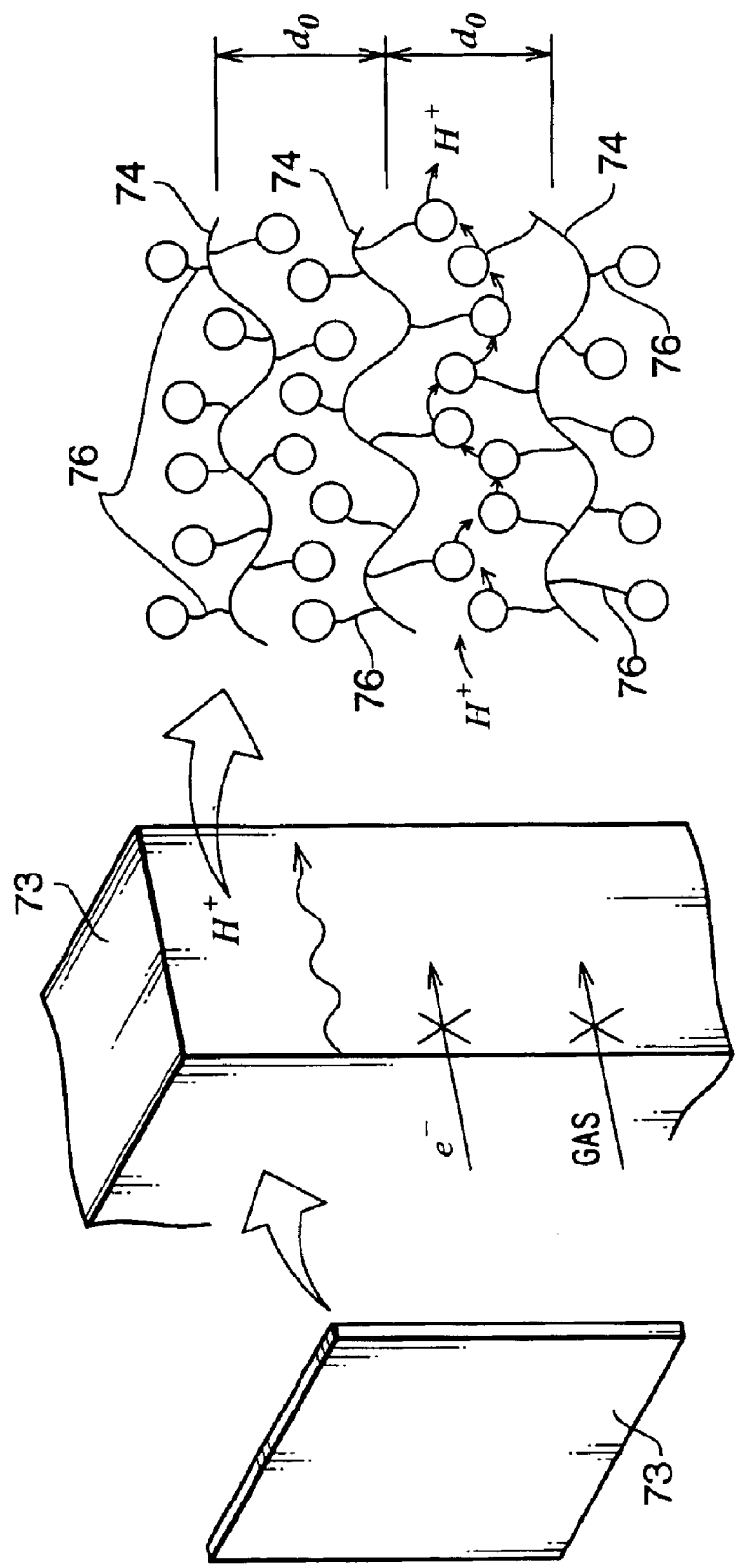
FIG. 12 is a diagram explaining an ion-exchange film, or a sample to be analyzed by the analyzing apparatus.

The ion-exchange film 73 used in the fuel cell have been made by synthesizing straight chains 74 and side chains 76, as illustrated in FIG. 12C. The straight chains 74 are spaced from one another at interval d0. The side chains 76 branch from the straight chains 74. In Nafion (trade name, manufactured by DuPont) known widely as an ion-exchange film, the straight chains 74 and the side chains 76 have such molecular structures as specified in FIG. 13.

In these molecular structures, the straight chains 74 are Teflon (registered trademark) groups and the side chains 76 are those formed by combining functional groups. Some of the functional groups shown in FIG. 13 may be removed or substituted by other functional groups, or other functional groups may be added, to alter the molecular structure of the ion-exchange film. The performance of the ion-exchange film can thereby be changed in various ways.

Having this specific molecular structure, the ion-exchange film 73 allows the passage of protons $H^+$ and does not allow the passage of electrons $e^-$ and gas, as illustrated in FIG. 12B. Namely, the film 73 performs ion exchange. The higher the ion-exchanging performance, the higher the performance of the fuel cell. The ion-exchanging performance is considered to change in accordance with the molecular structure shown in FIG. 12C. More specifically, it is influenced by the interval d0 between the straight chains, the arrangement of the side chains 76, and the like.

The sample 18, or ion-exchange film 73, is inserted into the inner space 31 of the sample chamber assembly 26. The film 73 is then clamped between the heat plates 23a and 23b, with the heat-resistant rubber ring 29a interposed between the film 73 and the plate 23a and the heat-resistant rubber ring 29b interposed between the film 73 and the plate 23b. The ion-exchange film 73 is thereby held at the prescribed position in the sample holder 12 shown in FIG. 1. Note that the ion-exchange film 73, i.e., sample 18, is far smaller than the size in which it is used in practice, or small enough to be inserted into the inner space 31.

The analysis was carried out at room temperature of 27° C. During the analysis, the heat plates 23a and 23b radiated heat. The temperature in the inner space 31 defined by the annular member 27, i.e., the temperature ambient to the ion-exchange film 73, was thereby changed to 50° C., 80° C., 100° C., 120° C., 150° C., 200° C., 230° C., and 270° C.

At each of the temperatures specified above, the small-angle X-ray scattering device 2 performed measurement on the ion-exchange film 73. More precisely, the X-ray source 4 generated an X-ray, which was applied to the ion-exchange film 73. Irradiated with the X-ray, the film 73 generated scattered radiation. The X-ray detector 13, or a storage phosphor plate, was exposed to the scattered radiation. Thus, an energy latent image was recorded in the storage phosphor plate 13.

To be more specific, as shown in FIG. 2, the X-ray source 4 emits an X-ray of high intensity, which is point-focused. The con-focal mirror 7 focuses the X-ray at the focus "f." The first slit 8 and second slit 9, which constitute a double slit, render the focused X-ray stable. The third slit 11 prevents the parasitic scattered radiation generated at the second slit 9 from irradiating the ion-exchange film 73 or the storage phosphor plate 13.

Figure 3:
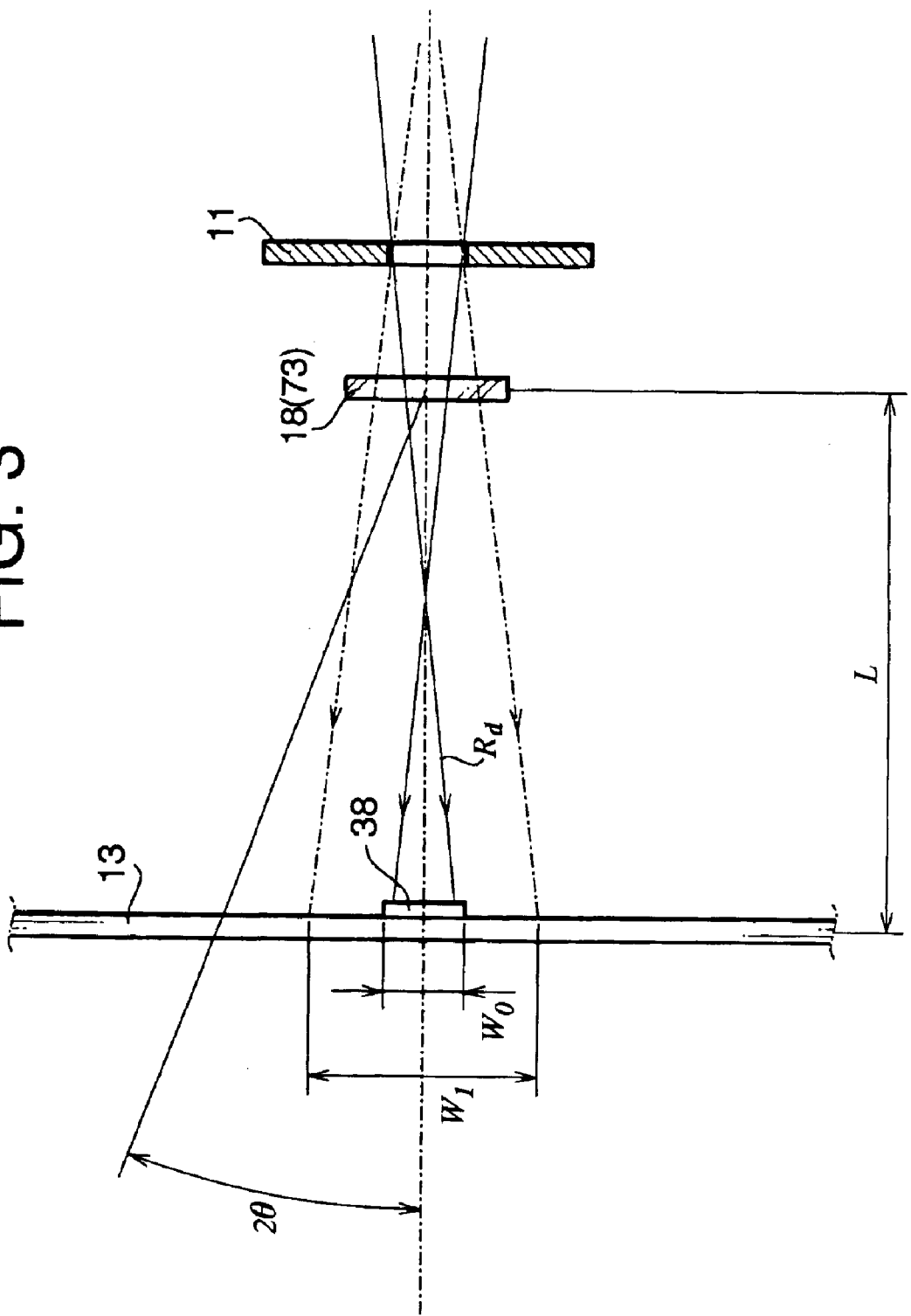
FIG. 3 is a magnified view illustrating the main components of the optical system shown in FIG. 2.

The X-ray passes through the third slit 11 and is applied to the ion-exchange film 73. Then, radiation scattered at an angle $2\theta$ that determined by the molecular structure of the film 73 is generated as shown in FIG. 3. The scattered radiation has intensity that depends on the molecular structure of the ion-exchange film 73. An energy latent image corresponding to the intensity of the scattered radiation is stored in that part of the storage phosphor plate 13 which has been irradiated with the scattered radiation.

As shown in FIG. 3, a direct beam stopper 38 is mounted on that region WO of the storage phosphor plate 13, toward which a direct beam Rd is applied. The stopper 38 prevents the direct beam Rd from directly illuminating the storage phosphor plate 13. In FIG. 3, "W1" denotes the region in which the parasitic scattered radiation generated at the second slit 9 shown in FIG. 2 reaches the storage phosphor plate 13, not blocked by the third slit 11.

In the regions W0 and W1 of the storage phosphor plate 13, the scattered radiation from the ion-exchange film 73 cannot be measured, bothered by the direct beam and the parasitic scattered radiation. Hence, the region of small angle $2\theta$, where the small-angle X-ray scattering device 4 according to this embodiment can measure X-rays, lies outside the region W1 in FIG. 3. The small angle ranges from 0.1° to 5°, or preferably from 0.1° to 4°.

To measure scattered radiation in such a small-angle region, it is necessary to narrow the slits 8, 9 and 11, thereby to render the X-ray extremely thin, and to lengthen the camera length "L". The ordinary X-ray measuring method using a wide-angle goniometer cannot measure the X-ray. Since the X-ray is made thin, it has low intensity when it reaches the ion-exchange film 73. It therefore takes a long time to measure the X-ray.

In the present embodiment, the con-focal mirror 7 focuses the X-ray emitted from the X-ray source 4 as illustrated in FIG. 2. Moreover, the X-ray from the X-ray source 4 is a point-focused one. That is, the X-ray applied to the ion-exchange film 73 is more intense than in the conventional X-ray measuring apparatus. With this embodiment, it is possible to apply scattered radiation of sufficient intensity to the storage phosphor plate 13, within a short time, for example about 20 minutes. In other words, the present embodiment can measure the X-ray within such a short time.

When the small-angle scattered radiation is measured at one temperature, such two-dimensional data about the diffracted X-ray emanating from the ion-exchange film 73 is recorded in the storage phosphor plate 13 in the form of an energy latent image. Thus, the degree of alignment of molecular structure pertaining to the ion-exchange film 73 can be evaluated in units of molecules. More specifically, the degree of alignment of the straight chains 74 and side chains 76 can be evaluated in units of molecules.

In the small-angle X-ray scattering device 2 of FIG. 1, a latent image pertaining to the ion-exchange film 73 is formed in the storage phosphor plate 13 by exposing the plate 13 to the scattered radiation at a temperature. Then, the storage phosphor plate 13 is removed from the small-angle X-ray scattering device 2 and set at a reading position of a reading device (not shown). The reading device scans the latent image, measuring the scattering angle (2θ) and intensity of the scattered radiation from the latent energy image stored in the storage phosphor plate 13. The reading device 41 is controlled by the CPU 56 and the like as is illustrated in FIG. 6.

Figure 7:
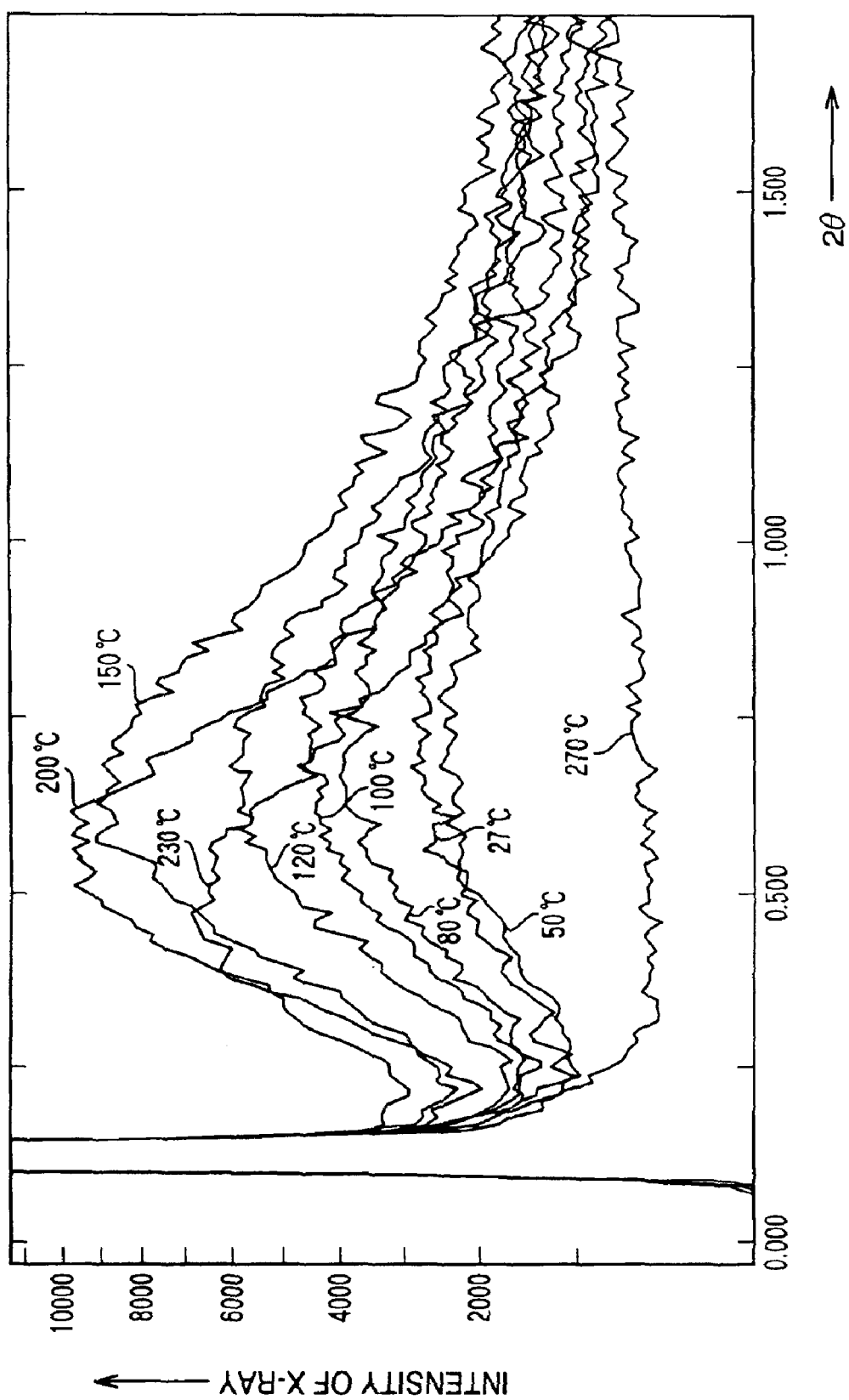
FIG. 7 is a graph representing the measuring results obtained by the X-ray small-angle scattering device shown in FIG. 1.

The CPU 56 shown in FIG. 6 stores the scattering angel (2θ) and intensity of the scattered radiation, thus measured, at a predetermined storage area in the RAM 57 or storage medium 59, in the form of, for example, a data table. The display 62 and the printer 63 can display and print the data table, as such a small-angle scattered-radiation graph as shown in FIG. 7. In the graph, the scattering angle (2θ) is plotted on the abscissa, and the X-ray intensity on the ordinate.

Assume that the ion-exchange film 73 is examined, while held as shown in FIG. 1 at room temperature (27° C.). Then, we have the small-angle scattering graph (27° C.) illustrated in FIG. 7. Next, the temperature of the ion-exchange film 73 is changed to 50° C., 80° C., 100° C., 120° C., 150° C., 200° C., 230° C., and 270° C. by the temperature control circuit 24 shown in FIG. 1. The small-angle X-ray scattering device 2 shown in FIG. 1 forms energy latent images for these temperatures. The energy latent images thus formed are stored in the storage phosphor plate 13. The reading device 41 reads the energy latent images from the plate 13. The CPU 56 processes the energy latent images read from the plate 13, generating the data items that represent the small-angle scattering curves for 50° C., 80° C., 100° C., 120° C., 150° C., 200° C., 230° C. and 270° C., all shown in FIG. 7.

Any person who observes the graph of FIG. 7 can recognize the peaks on these small-angle scattering curves and can read the X-ray intensities at the peaks. The positions of the peaks and the X-ray intensities at the peaks can be attributed to the changes that the ion-exchange film 73 undergoes in terms of molecular structure (FIG. 12C and FIG. 13) as its temperature changes while it remains dry. Thus, the observer of the graph of FIG. 7 can determine the molecular structure of the ion-exchange film 73 from the changes in the positions of the peaks and the changes in the X-ray intensities at the peaks.

In the analyzing apparatus 1 of FIG. 1, the CPU 56 shown in FIG. 6 causes the mass spectrometer 3 to measure the mass number of gas in accordance with a program, at the same time it causes the small-angle X-ray scattering device 2 to store energy latent images into the storage phosphor plate 13. In this embodiment, the sample holder 12 having a gas sampling structure as shown in FIG. 5 is set at the sample position, that is, the X-ray path in the small-angle X-ray scattering device 2. This embodiment thus can measure X-rays scattered at small angles and the mass number of the gas at the same time.

That is, carrier gas is introduced into the inner space 31 via the gas intake port 32 as shown in FIG. 5, at the same time an X-ray is applied to the ion-exchange film 73, as shown in FIG. 1, to detect the X-ray scattered at a small angle. Any gas the ion-exchange film 73 generates is supplied to the mass spectrometer 3 shown in FIG. 1 and subjected to mass analysis through the gas exhaust port 33.

Figure 8:
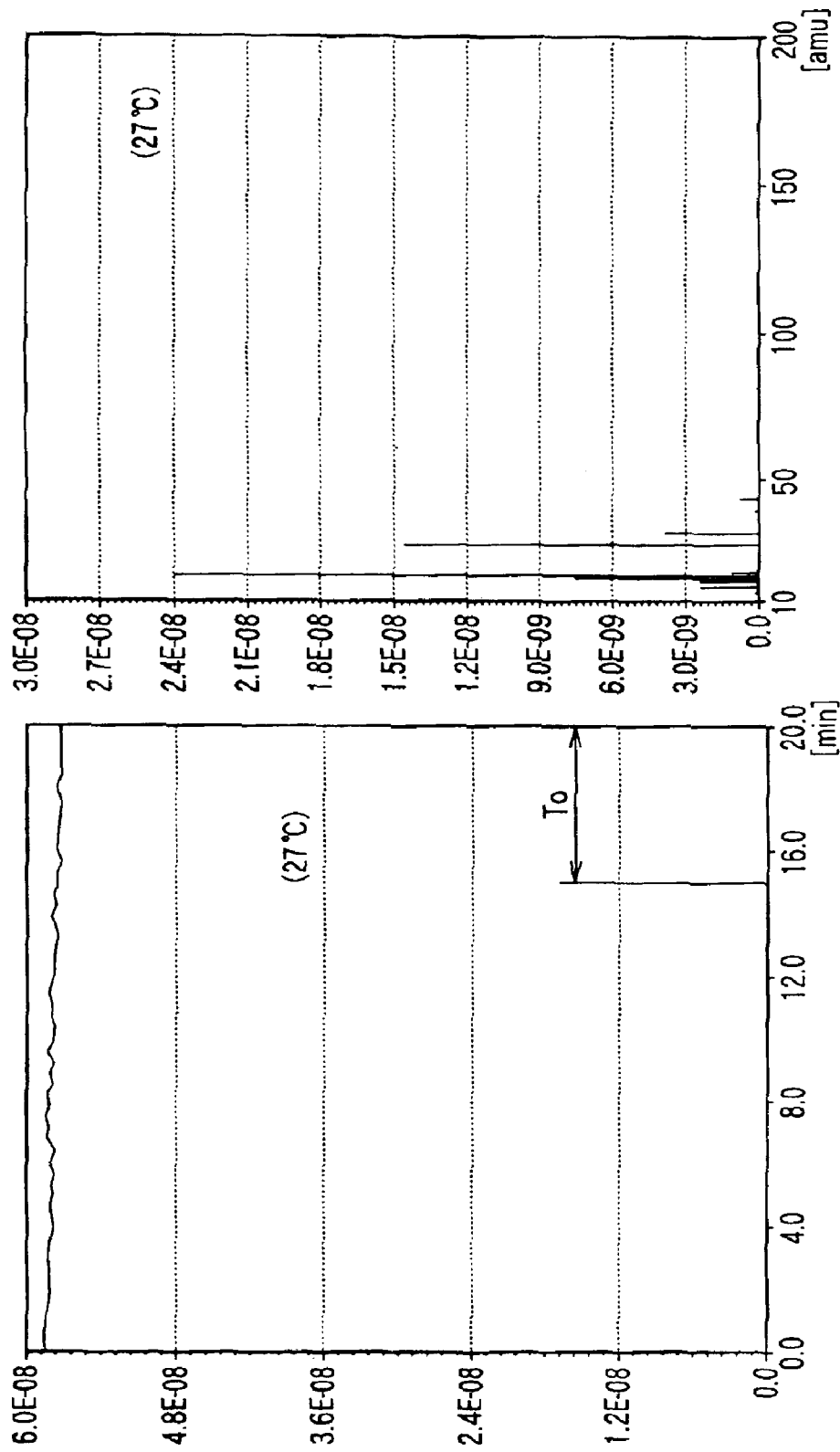
FIG. 8 is a graph illustrating the measuring results obtained by the mass spectrometer shown in FIG. 1.
Figure 9:
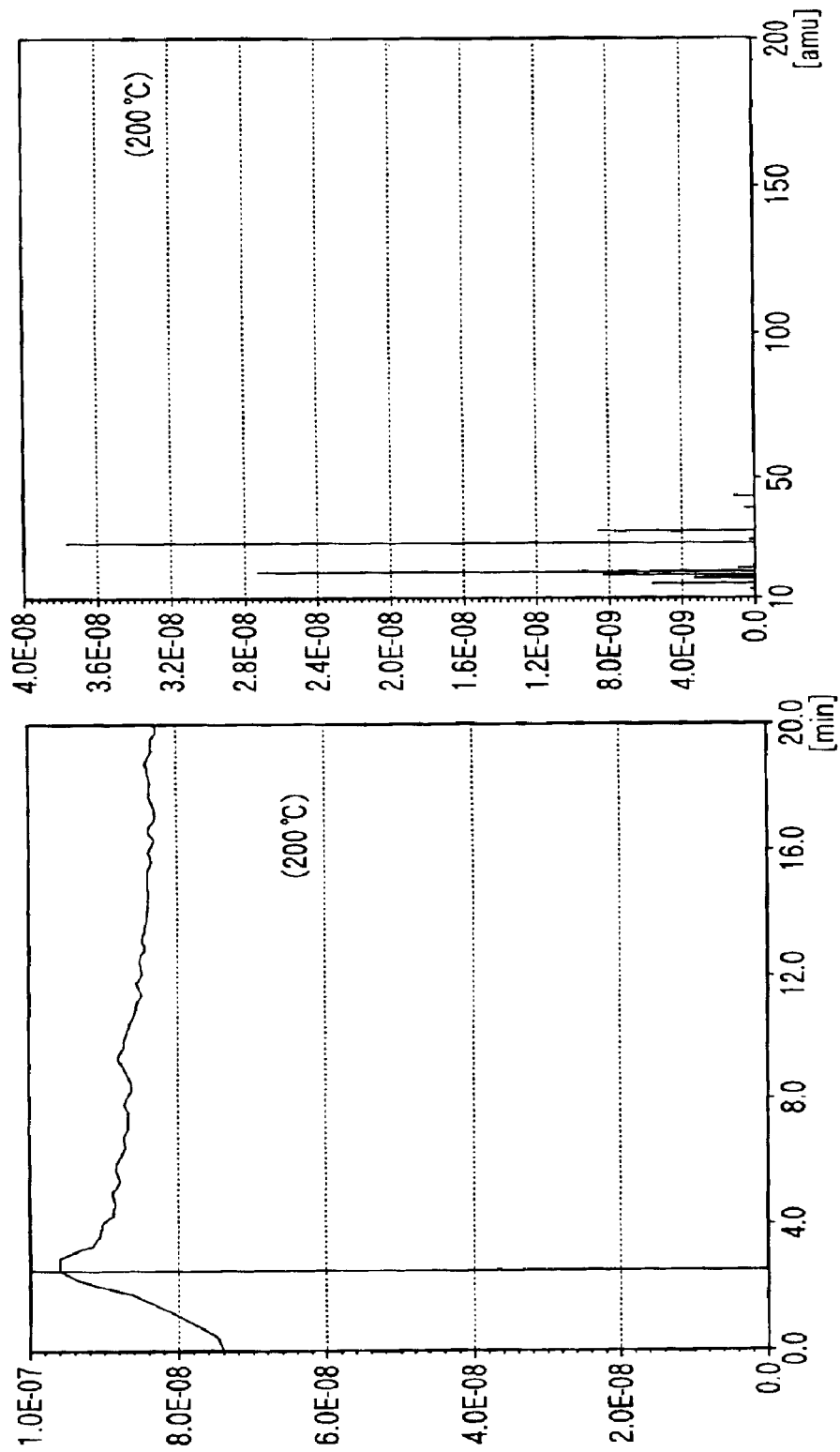
FIG. 9 is a graph representing the other measuring results obtained by the mass spectrometer shown in FIG. 1.
Figure 10:
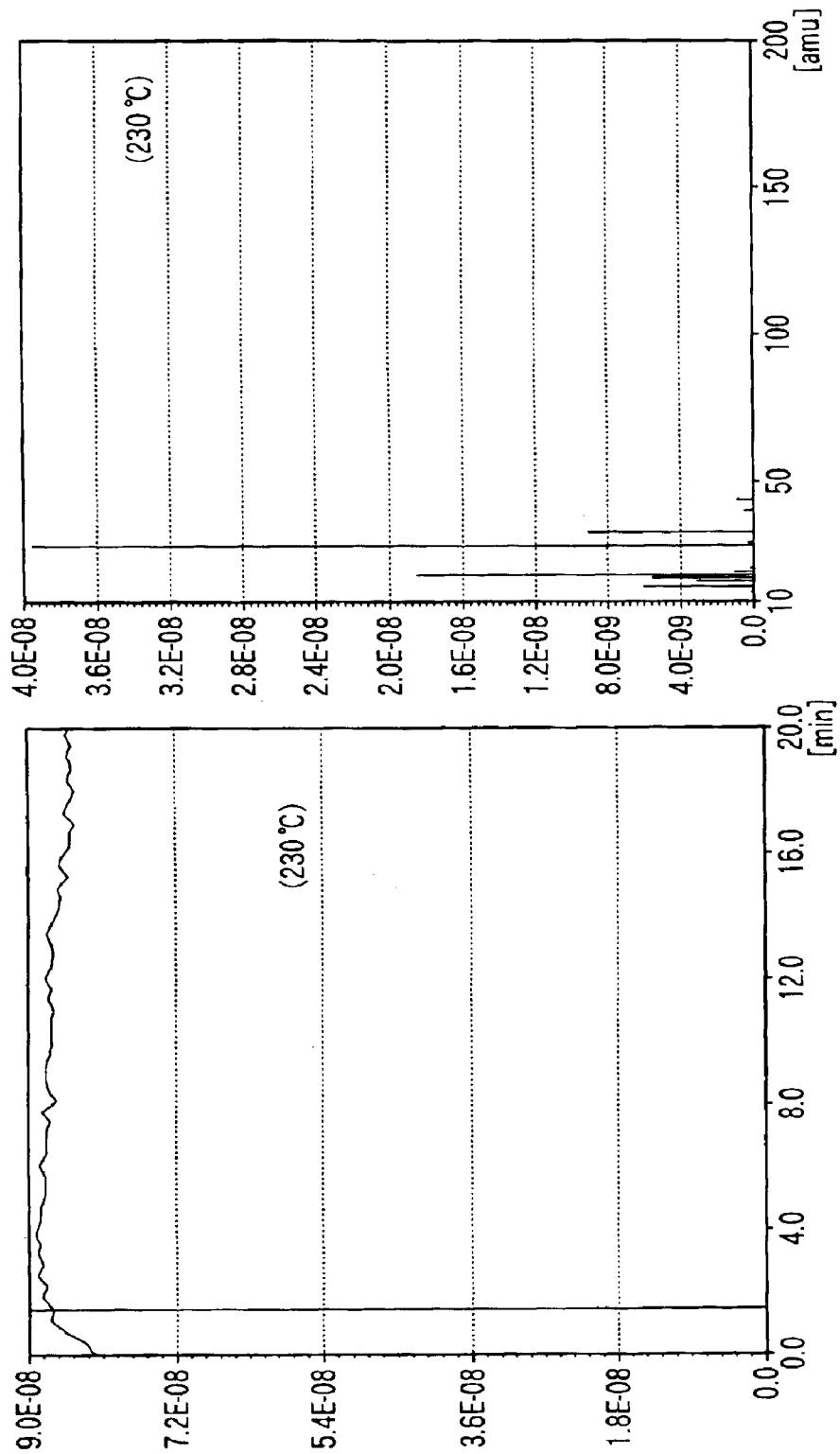
FIG. 10 is a graph displaying still other measuring results obtained by the mass spectrometer shown in FIG. 1.
Figure 11:
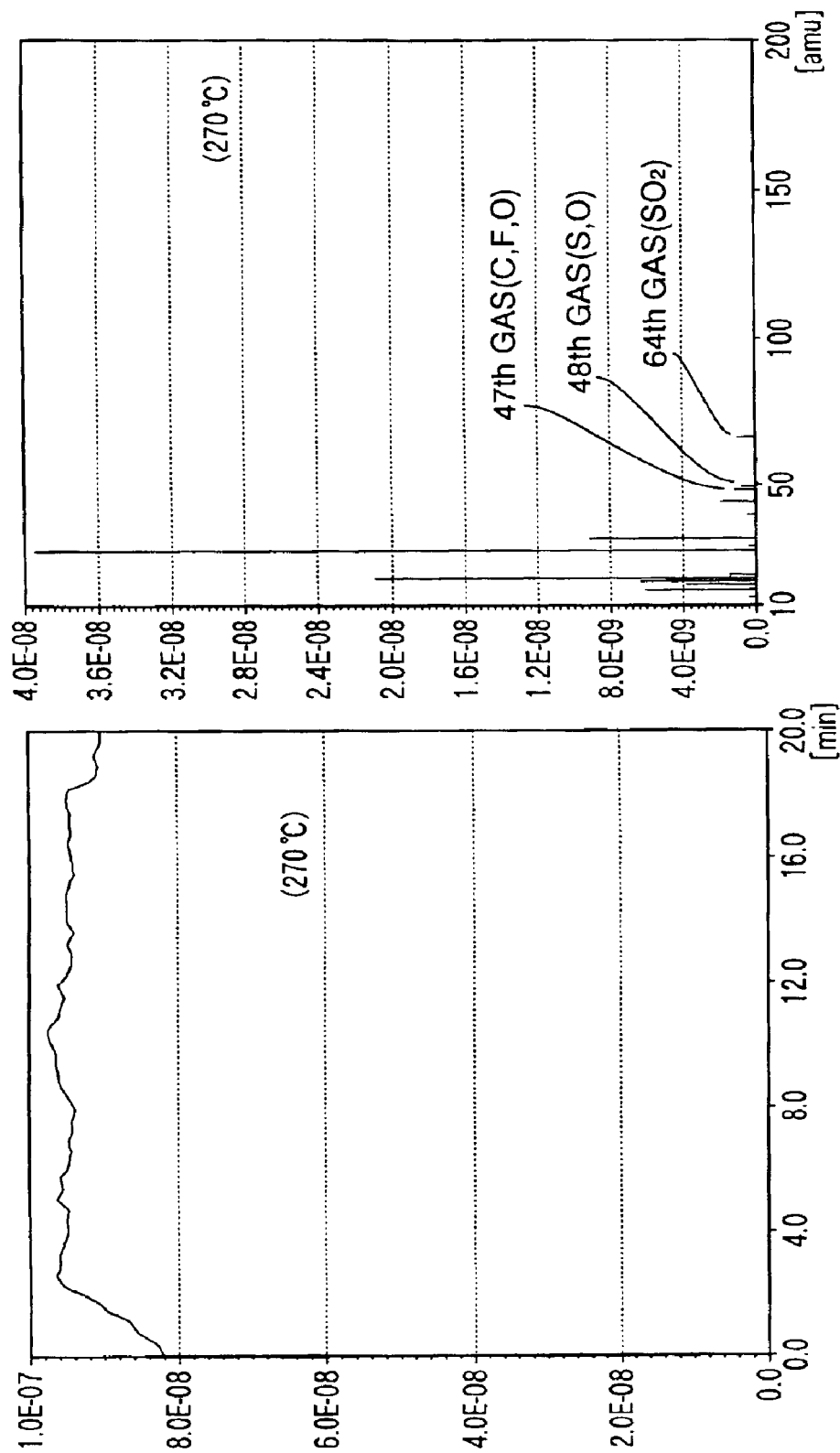
FIG. 11 is a graph illustrating other measuring results obtained by the mass spectrometer shown in FIG. 1.

FIG. 8 illustrates the results of the mass analysis carried out at 27° C. FIG. 9 represents the results of the mass analysis performed at 200° C. FIG. 10 shows the results of the mass analysis effected at 230° C. FIG. 11 displays the results of the mass analysis carried out at 270° C. FIGS. 8 to 11 consist of two bar graphs each. The left-hand graph indicates how the amount of the gas (plotted on the ordinate) generated from the ion-exchange film 73 varies with time (min., plotted on the abscissa). The right-hand graph shows how the amount of the gas (plotted on the ordinate) varies with the mass number of gas (plotted on the abscissa).

As seen from, for example, the left-hand graph in FIG. 8, the mass analysis is performed for about 20 minutes. The X-ray scattered at a small angle is measured for a period "T0" that ends about five minutes before the end of the mass analysis.

In this embodiment, the small-angle X-ray scattered-radiation graph of FIG. 7 and the mass-analysis data shown in FIGS. 8 to 11 can be obtained at the same time. From The graph and the data it is possible to determine the following.

From the graph of FIG. 7 it is observed that the peak gradually moves to the small-angle side and becomes higher as the temperature rises from 27° C. to 50° C., 80° C., 100° C., 120° C., 150° C., and 200° C. This can be attributed to the change in the molecular structure of the ion-exchange film 73, which occurs because the side chains 76 shown in FIG. 12C are gradually aligned as the temperature rises.

When the temperature rises from 200° C. to 230° C. and then to 270° C., the peak abruptly falls as seen from FIG. 7. The peak no longer exists at 270° C. The small-angle X-ray scattered-radiation graph alone cannot help to determine whether this phenomenon has resulted from the change in the molecular structure of the ion-exchange film 73 or any other possible change.

The mass-analysis data shown in FIGS. 8 to 11 reveal that the data item acquired at 270° C. is quite different from the data items acquired at any other temperature. The right-hand graph in FIG. 11 shows that 47th gases, 48th gases and 64th gas have generated, which have not generated at any temperatures lower than 270° C. The 47th gases are "C" (carbon) gas, "F" (fluorine) gas and "O" (oxygen) gas, the 48th gases are "S" (sulfur) gas and "O" (oxygen) gas. The 64th gas is $SO_2$ (sulfur dioxide) gas.

Figure 13:
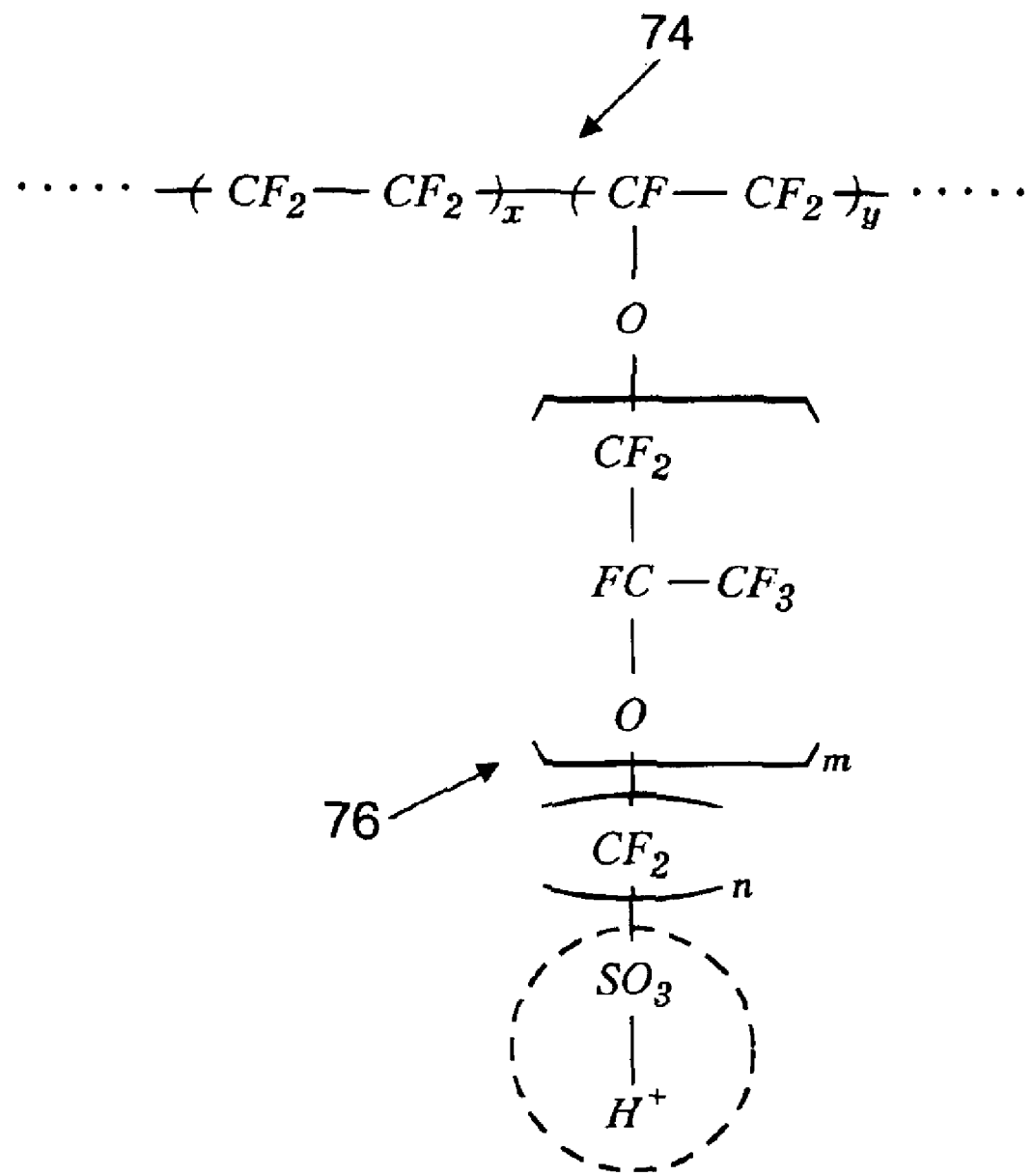
FIG. 13 is a structural formula of the ion-exchange film.

Consider this result in conjunction with the structural formula of the ion-exchange film 73, shown in FIG. 13. Then, it can be clearly understood that the functional group has been liberated due to pyrolysis at the temperature of 270° C. In view of this finding and the small-angle X-ray scattered-radiation graph of FIG. 7, we can determine two things. First, no change in terms of kinds of gases occurred at temperature from 27° C. to 230° C. Second, the peak changed in position and value as shown in FIG. 7 because the molecular structure of the ion-exchange film changed as the temperature rose. On the other hand, the change observed in the graph of FIG. 7, which took place as the temperature rose from 230° C. to 270° C., can be attributed to the pyrolysis of the side chains 76 (FIG. 13), not the change in the molecular structure of the ion-exchange film 73.

Thus, the analyzing apparatus according to this embodiment can help to determined precisely what change the sample undergoes as its temperature rises, from the changes in the position and value of the peak shown in the small-angle X-ray scattered-radiation graph and the data obtained by the mass analysis and representing the thermal hysteresis of the sample. The data acquired by the mass analysis can also reveal which part of the organic compound (e.g., the side chains) is responsible for the peak in the small-angle X-ray scattering graph.

The present embodiment can measure X-rays scattered at small angles, within a very short time for one of two reasons, or for both reasons; First, the con-focal mirror 7 provides an X-ray of high intensity. Second, the storage phosphor plate 13, or two-dimensional X-ray detector, detects the scattered X-rays coming from the sample 18, in the form of two-dimensional data.

The conventional small-angle X-ray scattering device that has no con-focal mirrors or no two-dimensional X-ray detectors requires tens of hours to measure scattered X-rays. By contrast, the small-angle X-ray scattering device 2 used in the present embodiment requires only about five minutes to detect scattered X-rays. The device 2 makes the embodiment, i.e., an analyzing apparatus, very advantageous for use in in-situ analysis. This is because the embodiment can determine the change that quickly occurs in the ion-exchange film as the ambient temperature of the film rises to high temperatures. Note that the conventional small-angle X-ray scattering device cannot be useful in in-situ analysis since it takes tens of hours to measure scattered X-rays.

The CPU 56 shown in FIG. 6 performs the following controls in accordance with a program. To be more specific, it stops the measuring performed by the small-angle X-ray scattering device 2, if at least one of four elements, C, F, S and O is detected by the mass spectrometer 3. That is, it stops the emission of the X-ray from the X-ray source 4 or closes the X-ray shutter 39 to prevent the X-ray from further travelling. Thus, after the ion-exchange film, or the sample, has been thermally decomposed, unnecessary measuring would not continue at all. This saves energy.

If necessary, the temperature control circuit 24 may change the condition of heating the sample 18 when the mass spectrometer 3 detects particular gas. Moreover, the condition in which the mass spectrometer 3 should analyze the gas generated from sample 18 may be changed on the basis of the measuring results obtained by the X-ray small-angle scattering device 2.

Other Embodiments

The present invention has been described, with reference to a preferred embodiment. Nonetheless, the embodiment does not limit the present invention. Various changes and modifications can be made within the scope of the invention, which will be defined in the claims.

For example, the small-angle X-ray scattering device 2 and the mass spectrometer 3, which are used respectively as the X-ray measuring means and second measuring means, may be replaced by other types of devices. More precisely, the X-ray measuring means may be, for example, a wide-angle X-ray diffracting device, and the second measuring means may be an NMR device or an IR device.

The sample that the embodiment analyzes is an ion-exchange film. The sample is not limited to an ion-exchange film. However, the embodiment is suitable for analyzing the molecular structures of organic compounds because it has an small-angle X-ray scattering device.

What is claimed is:

1. An analyzing apparatus comprising:

a small-angle X-ray scattering device that can detect X-rays scattered at a small angle to an axis of an X-ray applied to a sample, wherein the small-angle X-ray scattering device comprises: an X-ray source for generating X-rays, an X-ray collecting means for focusing X-rays at one point, and a two-dimensional X-ray detector for detecting X-rays at various points in a plane;

a mass spectrometer capable of measuring the mass number of gas generated by the sample;

sample-holding means for holding the sample at a position which is common to the small-angle X-ray scattering device and the mass spectrometer, wherein the sample-holding means is connected to provide the gas generated by the sample to the mass spectrometer using a carrier gas;

sample temperature-controlling means for controlling a temperature of the sample; and control means for controlling the small-angle X-ray scattering device and the mass spectrometer, causing the same to detect the X-rays and analyze the gas generated by the sample at the same time.

2. An analyzing apparatus according to claim 1, wherein the sample-holding means holds the sample and is arranged on an X-ray path in the small-angle X-ray scattering device, the X-rays are applied to the sample held in the sample-holding means, the X-rays generated by the sample are emitted outside the sample-holding means, and the gas generated from the sample are discharged outside the sample-holding means.

3. An analyzing apparatus according to claim 2 wherein the sample-holding means comprises:

an annular member defining a space for holding the sample, a pair of shield members that contact the front and back sides of the annular member and shield the space from outside, and a gas passage that connects the space in the annular member to the space outside the annular member.

4. An analyzing apparatus according to claim 3, further comprising pressing means that presses the shield members onto the annular member.

5. An analyzing apparatus according to claim 4, which further comprises sample temperature-controlling means for controlling a temperature of the sample, and in which control means changes a condition of controlling the temperature of the sample, in accordance with results of the measuring performed by the mass spectrometer and/or results of the measuring performed by the small-angle X-ray scattering device.

6. The analyzing apparatus according to claim 1, further comprising control means for controlling the small-angle X-ray scattering device, causing the same to detect the X-rays, in accordance with results of analysis performed by the mass spectrometer, or for controlling the mass spectrometer, causing the same to analyze the gas generated by the sample, in accordance with results of measuring performed by the small-angle X-ray scattering device.

7. An analyzing method comprising the steps of:

placing a sample at a position which is common to a small-angle X-ray scattering device and a mass spectrometer, wherein the small-angle X-ray scattering device is capable of detecting X-rays scattered at a small angle to an axis of an X-ray applied to the sample, and the mass spectrometer is capable of measuring the mass number of gas generated by the sample;

applying X-rays to the sample through an X-ray collecting means for focusing X-rays at one point;

detecting X-rays generated by the sample using a two-dimensional X-ray detector for detecting X-rays at various points in a plane, to measure the X-rays;

providing the gas generated by the sample to the mass spectrometer using a carrier gas; and analyzing the gas generated by the sample at the same time the X-ray is measured.

8. An analyzing apparatus comprising:

X-ray measuring means for applying X-rays to a sample and detecting X-rays generated by the sample;

a mass spectrometer capable of measuring the mass number of gas generated by the sample;

sample-holding means for holding the sample at a position which is common to X-ray measuring means and the mass spectrometer;

sample temperature-controlling means for controlling a temperature of the sample; and control means for controlling the X-ray measuring means and the mass spectrometer, causing the same to detect the X-rays and analyze the gas at the same time;

wherein the sample-holding means holds the sample and is arranged on an X-ray path in the X-ray measuring means, the X-rays are applied to the sample held in the sample-holding means, the X-rays generated by the sample are emitted outside the sample-holding means, and the gas generated by the sample are discharged outside the sample-holding means;

wherein the sample-holding means comprises:

an annular member defining a space for holding the sample;

a pair of shield members that contact the front and back sides of the annular member and shield the space from outside; and a gas passage that connects the space in the annular member to the space outside the annular member, further comprising pressing means that presses the shield members onto the annular member.

* * * * *